United States Patent
Guastella et al.

[19]

[11] Patent Number: 5,931,799
[45] Date of Patent: Aug. 3, 1999

[54] PARASEPTAL SPLINT FOR USE IN SURGICAL NASAL SEPTOPLASTY AND SEPTOVALVULOPLASTY

[76] Inventors: Claudio Guastella, Via B. Brin, 2-20149 Milan, Italy; Mario Mantovani, Via Santa Marta, 14-20123 Milan, Italy

[21] Appl. No.: 08/895,869

[22] Filed: Jul. 17, 1997

[30] Foreign Application Priority Data

Jul. 26, 1996 [IT] Italy ................................ MI96A01604

[51] Int. Cl.⁶ ................................ A61F 5/00; A61F 9/00; A61M 29/00
[52] U.S. Cl. ................................ 602/6; 128/858; 606/199
[58] Field of Search .................... 602/6, 17; 606/704.45, 606/199; 128/848, 858; 623/10

[56] References Cited

U.S. PATENT DOCUMENTS

| | | | |
|---|---|---|---|
| 2,265,387 | 12/1941 | McMillin | 606/199 |
| 3,935,859 | 2/1976 | Doyle | 606/199 |
| 4,105,035 | 8/1978 | Rella | 606/199 |
| 4,340,040 | 7/1982 | Straith | 606/204.45 |
| 4,592,357 | 6/1986 | Ersek | 606/199 |
| 5,022,389 | 6/1991 | Brennan | 128/858 X |
| 5,094,233 | 3/1992 | Brennan | 602/6 |
| 5,350,396 | 9/1994 | Eliachar | 606/199 |
| 5,479,944 | 1/1996 | Petruson | 128/858 |
| 5,599,284 | 2/1997 | Shea | 602/17 |

*Primary Examiner*—Richard J. Apley
*Assistant Examiner*—Denise Pothier
*Attorney, Agent, or Firm*—Guido Modiano; Albert Josif

[57] ABSTRACT

A paraseptal splint for use in surgical nasal septoplasties and septovalvuloplasties. The splint comprises a laminar body made of biocompatible material which has a posterior portion meant to be arranged paraseptally in the nasal fossa and, in the medioposterior septal region, and an anterior wing meant to be arranged in the vestibular region, in the valvular region and in the anterior septal portion of the nose. The anterior wing has an anterosuperior portion which is prefolded, or meant to be folded, with respect to the plane of arrangement of the remaining part of the laminar body, at an angle which corresponds to the anatomical angle between the septal cartilage and the triangular cartilage in the valvular region of the nose.

8 Claims, 2 Drawing Sheets

PARASEPTAL SPLINT FOR USE IN SURGICAL NASAL SEPTOPLASTY AND SEPTOVALVULOPLASTY

BACKGROUND OF THE INVENTION

The present invention relates to a paraseptal splint for use in surgical nasal septoplasty and septovalvuloplasty.

It is known that functional or anatomical modifications of the nasal valve considerably alter nasal physiology and cause severe obstructive conditions.

Owing to the functional importance of this anatomical region, in recent years many surgical techniques have been developed to reestablish the physiological valvular angle, such as resection of the dorsal portion of the alar cartilages, chondrotomy of the junction between the triangular cartilage and the nasal septum, plastic surgery of the triangular cartilages, plastic surgery of the alar cartilages.

So-called paraseptal splints are conventionally used in nasal surgery. These paraseptal splints support the septum after septoplasties and also allow early tampon removal and control of axial alignment of the reconstructed septum and at the same time reduce the risk of septal hematoma.

Currently available paraseptal splints are made of biocompatible material, generally Teflon, and are shaped substantially like an ellipse which is divided into two portions by a cut which runs through the body of the splint and affects almost all of its major axis. These splints are meant to be arranged in the nasal fossae paraseptally on both surfaces of the septal mucous membrane.

Although these splints effectively support the nasal septum, they are ineffective as regards any interaction on the triangular cartilage and scarcely effective in the valvular region as a whole.

The use of these splints has furthermore pointed out some problems, such as the possibility of lesions of the mucous membranes of the patient during insertion and extraction, reduced maneuverability of said splints, and difficulty in achieving the overlap of the two portions of the posterior region of the splint during insertion.

SUMMARY OF THE INVENTION

The aim of the present invention is to solve the above problems by providing a paraseptal splint which effectively supports the structures of the valvular and septal region during their healing following septoplasties and septovalvuloplasties, limiting the risk of contracture of scar tissue and subsequent restenosis of the nasal valve.

Within the scope of this aim, an object of the present invention is to provide a paraseptal splint which is easy to use and avoids the possibility of lesions of the mucous membranes during insertion or extraction.

Another object of the invention is to provide a paraseptal splint which prevents the onset of synechiae in the valvular region.

Another object of the invention is to provide a paraseptal splint which also allows to protect the septal mucous membrane in the anterior portion, stabilizing the columellar region and avoiding traumatisms induced by patient self-manipulation.

This aim, these objects and others which will become apparent hereinafter are achieved by a paraseptal splint for use in surgical septoplasties and septovalvuloplasties, which comprises a laminar body made of biocompatible material which has a posterior portion adapted to be arranged paraseptally in the nasal fossa, in the medioposterior septal region, and an anterior wing meant to be arranged in the vestibular region, in the valvular region and in the anterior septal portion of the nose; in which said anterior wing has an anterosuperior portion which is pre-folded, or adapted to be folded, with respect to the plane of arrangement of the remaining part of the laminar body, at an angle which corresponds to the anatomical angle between the septal cartilage and the triangular cartilage in the valvular region of the nose.

BRIEF DESCRIPTION OF THE DRAWINGS

Further characteristics and advantages of the present invention will become apparent from the following detailed description of a preferred but not exclusive embodiment of the paraseptal splint according to the invention, illustrated by way of non-limitative example in the accompanying drawings, wherein.

DESCRIPTION OF THE PREFERRED EMBODIMENTS

Figure 1:
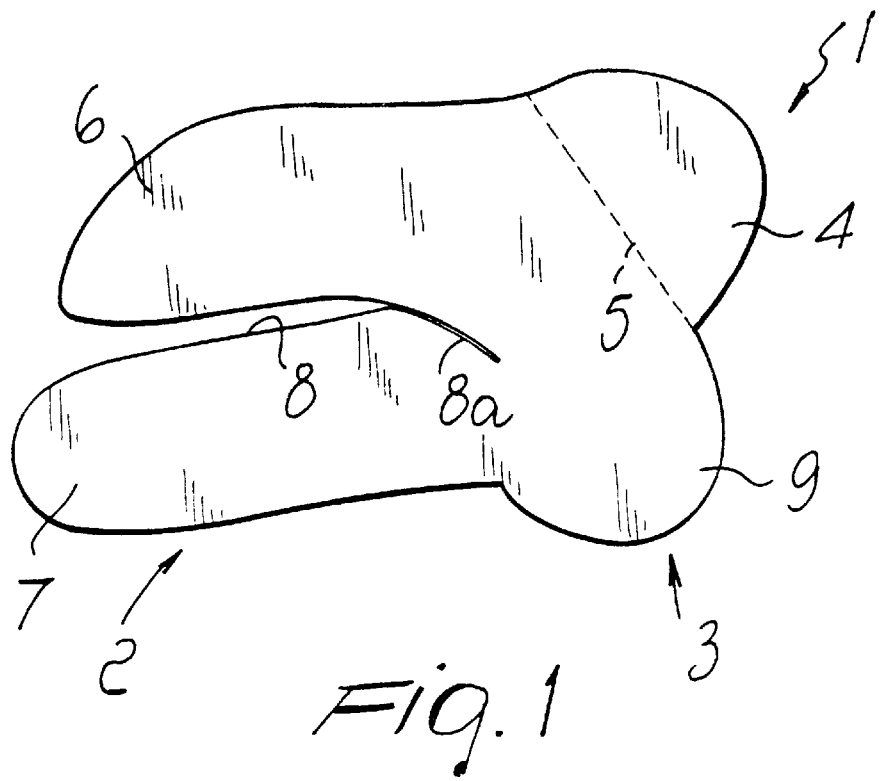
FIG. 1 is a view of the paraseptal splint according to the invention, before folding the anterosuperior portion of the front wing.

With reference to the above figures, the paraseptal splint according to the invention, generally designated by the reference numeral 1, comprises a laminar body made of biocompatible material, such as for example Teflon or other conventional biocompatible material, which has a posterior portion 2 meant to be arranged in a nasal fossa paraseptally in the medioposterior septal region, and an anterior wing 3 meant to be arranged in the vestibular region, in the valvular region and in the anterior septal region of the nose.

According to the invention, the anterior wing 3 is provided with an anterosuperior portion 4 which is pre-folded or meant to be folded along a line 5, shown in dashes in FIG. 1, with respect to the plane of arrangement of the remaining part of the laminar body at an angle which corresponds to the anatomical angle between the septal cartilage and the triangular cartilage in the valvular region of the nose, which usually lies substantially between 10° and 150°.

Advantageously, the posterior portion 2 is divided into two arms 6 and 7 by an anteroposterior median slot 8 which affects the posterior portion 2 and ends towards the inside of the laminar body with a slit 8a which curves downward.

Figure 2:
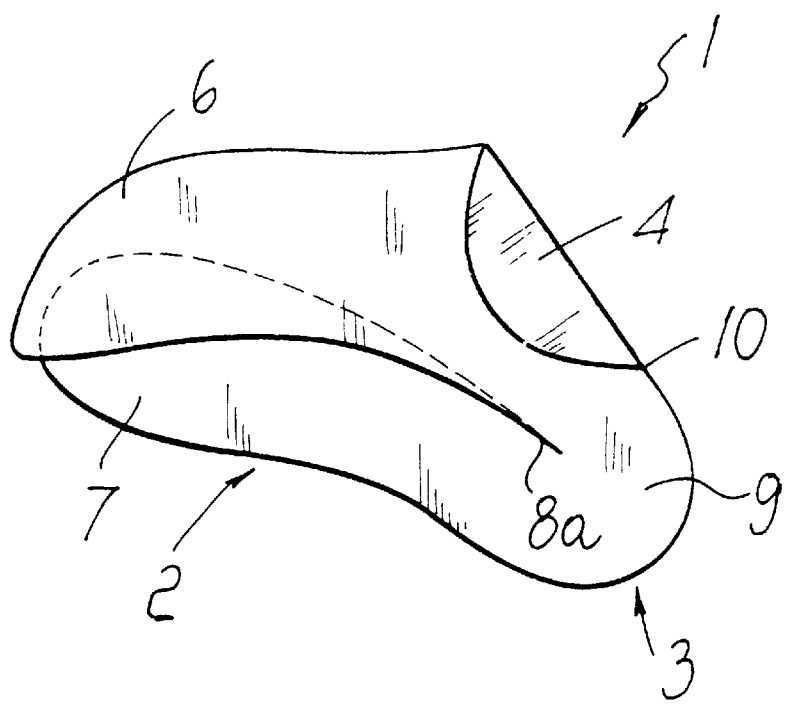
FIG. 2 is a view of the paraseptal splint according to the invention, in the condition in which it is inserted in the nose of the patient.
Figure 3:
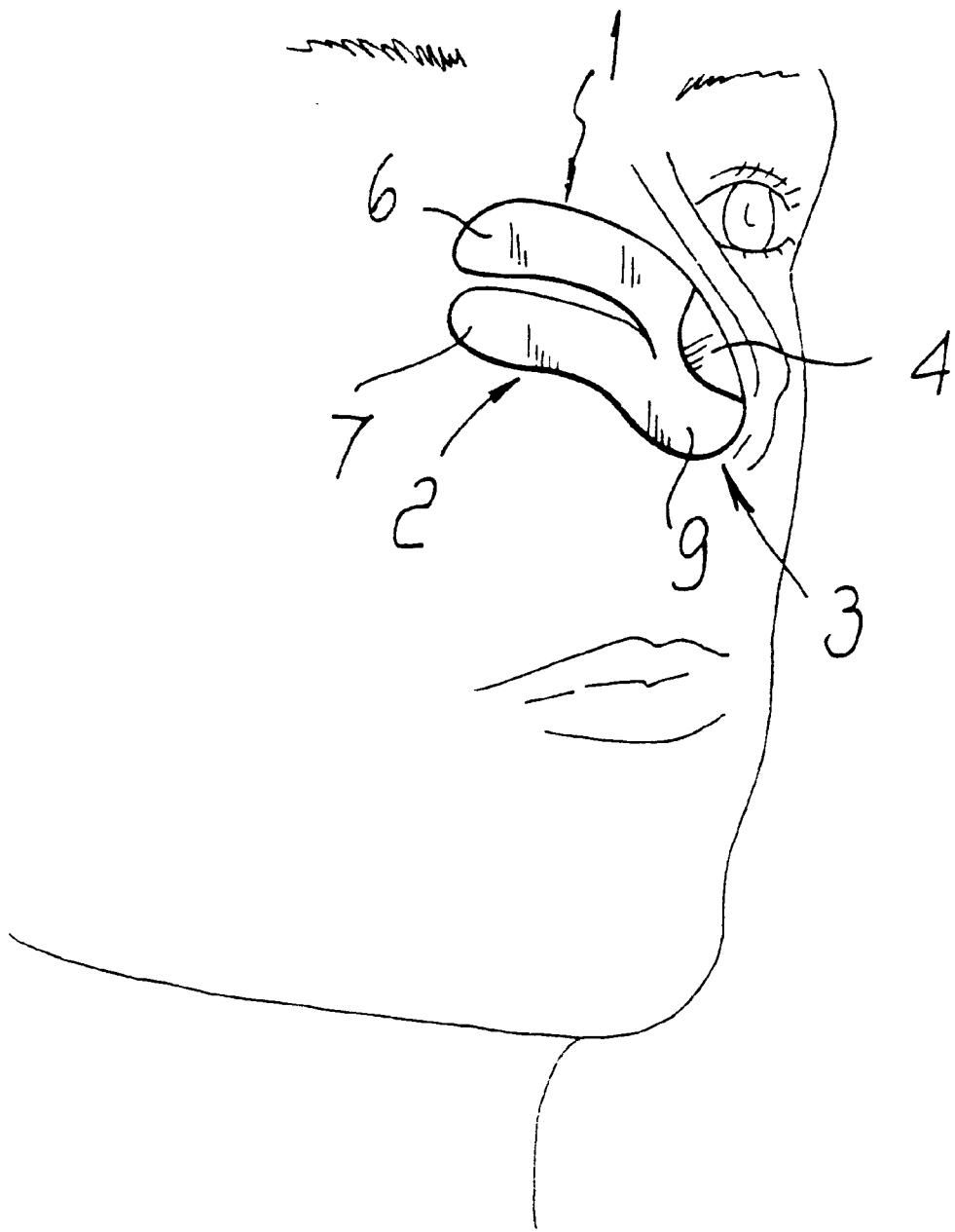
FIG. 3 is a view of the paraseptal splint according to the invention in situ.

The particular configuration of the slot 8 and of its end part 8a produces excellent elastic deformability of the splint when overlapping the two arms 6 and 7, as shown in FIG. 2.

Conveniently, again to facilitate the operations for inserting and extracting the splint with respect to the nose of the patient, the lower arm 7 has a rounded free end and the upper arm 6 has a free end which is at least partially aligned with the free end of the lower arm 7.

The front wing 3 furthermore has an anteroinferior portion 9 which is meant to laterally overlap the anterior region of the nasal septum.

The anterosuperior portion 4 and the anteroinferior portion 9 have a curved profile which protrudes downward and upward from the contour of the remaining part of the laminar body 2.

The portions 4 and 9 are furthermore separated by an anterior median recess 10 of the laminar body.

Use of the splint according to the invention is as follows.

The splint 1 is inserted, optionally after being reshaped by cutting, according to the dimensions and configuration of the nasal fossae, after folding the anterosuperior portion 4 along the line 5 and after moving the upper arm 6 towards the lower arm 7 to facilitate insertion.

The angle formed by the anterosuperior portion 4 with respect to the remaining part of the body of the splint is such as to produce perfect adaptation of the splint to the valvular region.

The anteroinferior portion 9 of the splint covers the septal mucous membrane in its anterior portion, which is usually affected by the hemitransfix incision. In this way excellent protection of this region is achieved as well as stabilization of the columellar region, and any traumatism due to patient self-manipulation is also avoided.

After insertion, a check is made to ensure that there are no sharp corners which might traumatize the mucous membrane and that the anterior edge of the anterior wing 3 is not covered by mucous membrane or does not directly affect any incisions in the mucous membrane performed during surgery but instead covers them.

The wing 3 is placed cranially with its anterosuperior portion 4 in contact with the valvular region with an aperture angle of approximately 10°–15°.

A splint is inserted in each nostril and it is preferably anchored by means of Cottle's bayonet forceps by using the fixing teeth. The nasal tampon helps to keep the splint in contact with the septovalvular mucous membrane after surgery.

The splints are fixed with one or two transfix sutures, preferably by using a non-absorbable monofilament.

According to requirements, the splints can be left in situ for 7 to 21 days.

For extraction, the splints are slightly rotated clockwise for the left nostril and counterclockwise for the right nostril, after eliminating the transfix fixing sutures.

This extraction is easier than that of conventional splints, since the presence of the fold of the anterosuperior portion 4 does not cause traumas to the upper nostril region.

The flexibility of the posterior portion of the splint, facilitated by the two arms 6 and 7, allows complete extraction thereof without problems.

In practice, it has been observed that the paraseptal splint according to the invention fully achieves the intended aim and objects, since it allows the healing of the septovalvular reparatory processes with guided cicatrization, avoiding any secondary valvular cicatricial stenoses.

Further advantages that arise from the use of paraseptal splints according to the invention are constituted by prolonged septal stabilization, prevention of septal hematomas, septal hemostasis, prevention of synechiae, early and easy tampon removal, reduction of scab formations, stabilization of the valve with a suitable angle, improved septal stabilization (especially cranially), stabilization of the tip of the nose, and prevention of lesions due to patient self-manipulation.

The paraseptal splint thus conceived is susceptible of numerous modifications and variations, all of which are within the scope of the inventive concept; all the details may furthermore be replaced with other technically equivalent elements.

In practice, the materials employed, so long as they are compatible with the specific use, as well as the dimensions, may be any according to requirements and to the state of the art.

What is claimed is:

1. A paraseptal splint for use in surgical septoplasties and septovalvuloplasties, consisting of a laminar body made of biocompatible material provided with
    a posterior portion adapted to be arranged alongside nasal septum within the nasal fossa and in the medioposterior septal region;
    an anterior wing extending from the posterior portion and adapted to be arranged in the vestibular and valvular region and in the anterior septal portion of the nose; wherein
    said anterior wing has an anterosuperior portion which is adapted to be folded with respect to the plane of arrangement of the remaining part of the laminar body, at an angle which corresponds to the anatomical angle between the septal cartilage and the triangular cartilage in the valvular region of the nose.

2. A paraseptal splint according to claim 1, wherein said laminar body is elastic and said posterior portion is divided into an upper and a lower arm by an anteroposterior median slot which affects said posterior portion.

3. A paraseptal splint according to claim 2, wherein the upper and lower arms have free ends at least partially aligned.

4. A paraseptal splint according to claim 2, wherein said lower arm is provided with a rounded free end.

5. A paraseptal splint according to claim 2, wherein said anteroposterior median slot is provided with an end having a downward-curving slit.

6. A paraseptal splint according to claim 1, wherein said anterior wing has an anteroinferior portion which is adapted to laterally overlap the anterior region of the nasal septum.

7. A paraseptal splint according to claim 6, wherein said anterior wing is provided with an anterosuperior portion and an anteroinferior portion having a curved profile.

8. A paraseptal splint according to claim 6, wherein said anterosuperior portion and said anteroinferior portion are separated by a medioanterior recess of the laminar body.

* * * * *